US008105239B2

(12) United States Patent
Specht

(10) Patent No.: US 8,105,239 B2
(45) Date of Patent: Jan. 31, 2012

(54) METHOD AND APPARATUS TO VISUALIZE THE CORONARY ARTERIES USING ULTRASOUND

(75) Inventor: Donald F. Specht, Los Altos, CA (US)

(73) Assignee: Maui Imaging, Inc., Sunnyvale, CA (US)

( * ) Notice: Subject to any disclaimer, the term of this patent is extended or adjusted under 35 U.S.C. 154(b) by 1106 days.

(21) Appl. No.: 11/532,013

(22) Filed: Sep. 14, 2006

(65) Prior Publication Data

US 2007/0238999 A1 Oct. 11, 2007

Related U.S. Application Data

(60) Provisional application No. 60/765,887, filed on Feb. 6, 2006.

(51) Int. Cl.
*A61B 8/14* (2006.01)

(52) U.S. Cl. ........ 600/446; 600/407; 600/437; 600/443; 600/445

(58) Field of Classification Search .......... 600/407–410, 600/413, 420, 424–426, 428, 431, 436, 437–450, 600/453–458; 358/447, 463; 706/1–8, 14–24; 345/619, 642, 643; 382/155–158, 254, 260, 382/261
See application file for complete search history.

(56) References Cited

U.S. PATENT DOCUMENTS

| 4,271,842 A | 6/1981 | Specht et al. |
| 4,501,279 A * | 2/1985 | Seo ............................... 600/456 |
| 4,682,497 A | 7/1987 | Sasaki |
| 4,893,628 A | 1/1990 | Angelsen |
| 5,442,462 A * | 8/1995 | Guissin ........................ 358/463 |
| 5,515,853 A | 5/1996 | Smith et al. |
| 5,522,393 A | 6/1996 | Phillips et al. |
| 5,675,550 A | 10/1997 | Ekhaus |
| 5,798,459 A * | 8/1998 | Ohba et al. ...................... 73/587 |

(Continued)

FOREIGN PATENT DOCUMENTS

WO WO 2006/114735 A1 11/2006

OTHER PUBLICATIONS

Sakas et al.; Preprocessing and volume rendering of 3D ultrasonic data; IEEE Computer Graphics and Applications; pp. 47-54, Jul. 1995.

(Continued)

*Primary Examiner* — Tse Chen
*Assistant Examiner* — Mark Remaly
(74) *Attorney, Agent, or Firm* — Shay Glenn LLP

(57) ABSTRACT

A non-invasive screening technique for visualizing coronary arteries which overcomes the problems of visualizing the curved arteries by projecting the three dimensional volume of the arteries onto a two dimensional screen. Blood filled areas such as the coronary arteries and veins, are highlighted to contrast with other nearby tissues using non-linear classification and segmentation techniques. Data is gathered as a sequence of 2D slices stored as a 3D volume. Software interpolates voxels intermediate to the slices. Wiener filtering or LMS spatial filtering can be implemented on each 2D scan to improve lateral resolution and reduce noise prior to the use of the scan data with the classification and segmentation algorithms. A traditional handheld ultrasound probe is employed to enable the technician to locate the area of interest, but a gyroscopic stabilizer is added to minimize unwanted variation on two axes of rotation.

23 Claims, 3 Drawing Sheets

U.S. PATENT DOCUMENTS

| | | | | |
|---|---|---|---|---|
| 5,876,342 | A | 3/1999 | Chen et al. | |
| 5,964,707 | A | 10/1999 | Fenster et al. | |
| 6,014,473 | A | 1/2000 | Hossack et al. | |
| 6,056,693 | A | 5/2000 | Haider | |
| 6,122,538 | A * | 9/2000 | Sliwa et al. | 600/407 |
| 6,148,095 | A | 11/2000 | Prause et al. | |
| 6,166,853 | A | 12/2000 | Sapia et al. | |
| 6,246,901 | B1 * | 6/2001 | Benaron | 600/431 |
| 6,324,453 | B1 * | 11/2001 | Breed et al. | 701/45 |
| 6,394,955 | B1 | 5/2002 | Perlitz | |
| 6,449,821 | B1 | 9/2002 | Sudol et al. | |
| 6,468,216 | B1 * | 10/2002 | Powers et al. | 600/443 |
| 6,471,650 | B2 | 10/2002 | Powers et al. | |
| 6,517,484 | B1 | 2/2003 | Wilk et al. | |
| 6,690,816 | B2 | 2/2004 | Aylward et al. | |
| 6,728,567 | B2 * | 4/2004 | Rather et al. | 600/407 |
| 6,755,787 | B2 | 6/2004 | Hossack et al. | |
| 6,780,152 | B2 | 8/2004 | Ustuner et al. | |
| 6,843,770 | B2 | 1/2005 | Sumanaweera | |
| 6,932,767 | B2 | 8/2005 | Landry et al. | |
| 7,033,320 | B2 | 4/2006 | Von Behren et al. | |
| 7,087,023 | B2 | 8/2006 | Daft et al. | |
| 7,313,053 | B2 | 12/2007 | Wodnicki | |
| 7,366,704 | B2 | 4/2008 | Reading et al. | |
| 7,402,136 | B2 | 7/2008 | Hossack et al. | |
| 7,410,469 | B1 | 8/2008 | Talish et al. | |
| 7,443,765 | B2 | 10/2008 | Thomenius et al. | |
| 7,447,535 | B2 | 11/2008 | Lavi | |
| 7,466,848 | B2 | 12/2008 | Metaxas et al. | |
| 7,474,778 | B2 | 1/2009 | Shinomura et al. | |
| 7,497,828 | B1 | 3/2009 | Wilk et al. | |
| 7,497,830 | B2 | 3/2009 | Li | |
| 7,510,529 | B2 | 3/2009 | Chou et al. | |
| 7,514,851 | B2 | 4/2009 | Wilser et al. | |
| 7,549,962 | B2 | 6/2009 | Dreschel et al. | |
| 7,574,026 | B2 | 8/2009 | Rasche et al. | |
| 7,787,680 | B2 | 8/2010 | Ahn et al. | |
| 2002/0035864 | A1 | 3/2002 | Paltieli et al. | |
| 2002/0087071 | A1 | 7/2002 | Schmitz et al. | |
| 2003/0028111 | A1 | 2/2003 | Vaezy et al. | |
| 2003/0040669 | A1 * | 2/2003 | Grass et al. | 600/407 |
| 2003/0228053 | A1 | 12/2003 | Li et al. | |
| 2004/0122313 | A1 | 6/2004 | Moore et al. | |
| 2004/0122322 | A1 | 6/2004 | Moore et al. | |
| 2004/0138565 | A1 | 7/2004 | Trucco | |
| 2005/0004449 | A1 | 1/2005 | Mitschke et al. | |
| 2005/0020918 | A1 | 1/2005 | Wilk et al. | |
| 2005/0053305 | A1 | 3/2005 | Li et al. | |
| 2005/0054910 | A1 | 3/2005 | Tremblay et al. | |
| 2005/0090743 | A1 * | 4/2005 | Kawashima et al. | 600/443 |
| 2005/0147297 | A1 | 7/2005 | McLaughlin et al. | |
| 2005/0281447 | A1 | 12/2005 | Moreau-Gobard et al. | |
| 2005/0288588 | A1 | 12/2005 | Weber et al. | |
| 2006/0062447 | A1 | 3/2006 | Rinck et al. | |
| 2006/0074315 | A1 * | 4/2006 | Liang et al. | 600/450 |
| 2006/0079759 | A1 | 4/2006 | Vaillant et al. | |
| 2006/0079778 | A1 | 4/2006 | Mo et al. | |
| 2006/0079782 | A1 | 4/2006 | Beach et al. | |
| 2007/0036414 | A1 | 2/2007 | Georgescu et al. | |
| 2007/0055155 | A1 | 3/2007 | Owen et al. | |
| 2007/0078345 | A1 | 4/2007 | Mo et al. | |
| 2007/0167752 | A1 | 7/2007 | Proulx et al. | |
| 2007/0232914 | A1 | 10/2007 | Chen et al. | |
| 2008/0103393 | A1 | 5/2008 | Specht | |
| 2008/0181479 | A1 | 7/2008 | Yang et al. | |
| 2008/0194958 | A1 | 8/2008 | Lee et al. | |
| 2008/0194959 | A1 | 8/2008 | Wang et al. | |
| 2008/0255452 | A1 | 10/2008 | Entrekin | |
| 2008/0269613 | A1 | 10/2008 | Summers et al. | |
| 2008/0294045 | A1 | 11/2008 | Ellington et al. | |
| 2008/0294050 | A1 | 11/2008 | Shinomura et al. | |
| 2008/0319317 | A1 | 12/2008 | Kamiyama et al. | |
| 2009/0016163 | A1 | 1/2009 | Freeman et al. | |
| 2009/0182237 | A1 | 7/2009 | Angelsen et al. | |
| 2009/0208080 | A1 | 8/2009 | Grau et al. | |
| 2010/0217124 | A1 | 8/2010 | Cooley | |

OTHER PUBLICATIONS

Widrow et al.; Adaptive signal processing; Prentice-Hall; Englewood Cliffs, NJ; pp. 99-137; 1985.

Cristianini et al.; An Introduction to Support Vector Machines; Cambridge University Press; pp. 93-111; 2000.

Haykin, Simon; Neural Networks: A Comprehensive Foundation (2nd Ed.); Prentice Hall; pp. 156-187; 1999.

Mark Angelo Sapia, Ph.D. Mutli-Dimensional Deconvolution of Optical Microscope and Ultrasound Imaging Using . . . Ph.D. Dissertation, University of Connecticut, 2000.

Sapia, et al. Ultrasound Image Deconvolution Using Adaptive Inverse Filtering 12th IEEE Symposium on Computer-Based Medical Systems, CBMS, 1999. pp. 248-253.

D. F. Specht, A General Regression Neural Network, IEEE Transactions on Neural Networks, vol. 2, No. 6, Nov. 1991.

D. F. Specht, Enhancements to Probabilistic Neural Networks, Proc. IEEE International Joint conference on Neural Networks, Baltimore, MD, Jun. 1992.

D. F. Specht & H. Romsdahl, Experience with Adaptive PNN and Adaptive GRNN, Proc. IEEE International Joint conference on neural Networks, vol. 2, pp. 1203-1208, Orlando, FL Jun. 1994.

D. F. Specht, GRNN with Double Clustering, Proc. IEEE International Joint conference on Neural Networks, Vancouver, Canada, Jul. 16-21, 2006.

M. Morrison & Y. Attikiouzel, A Probablilistic Neural Network Based on Image Segmentation Network . . . ,Proc. conf. Neural Networks, Baltimore, MD 1992, vol. 3, pp. 60-65.

Maria J. Ledesma-Carbayo et al, Spatio=Temporal nonrigid Registration for Ultrasound Cardiac Motion Estimation, IEEE Trans. on Medical Imaging, vol. 24, No. 9, Sep. 2005.

Seemantini Nadkarni, Cardiac Motion Synchronization for 3D . . . Ph.D. Dissertation, Unv of W. Ontario 2005.

D. F. Specht, Blind Deconvolution of Motion Blur using LMS Inverse Filtering, Lockheed Independent Research, Unpublished 1976.

S. W. Smith et al, High-Speed Ultrasound Volumetric Imaging System . . . IEEE Transactions on Ultrasonics . . . vol. 38, No. 2, Mar. 1991 pp. 100-108.

O. T. Von Ramm et al, High-Speed Ultrasound Volumetric Imaging System . . . IEEE Transactions on Ultrasonics . . . vol. 38, No. 2, Mar. 1991, pp. 109-115.

P. N. T. Wells, Biomedical Ultrasonics, Academic Press, London, New York, San Francisco, 1977, pp. 124-125.

Harvey Feigenbaum, MD, Echocardiography, 5th Edition, Lippincott Williams & Wilkins, Philadelphia, 1993, pp. 428, 484.

Smith et al.; U.S. Appl. No. 12/760,375 entitled "Universal Multiple Aperture Medical Ultrasound Probe," filed Apr. 14, 2010.

Specht et al.; U.S. Appl. No. 12/760,327 entitled "Multiple Aperture Ultrasound Array Alignment Fixture," filed Apr. 14, 2010.

Leotta et al.; Quantitative three-dimensional echocardiography by rapid imaging . . . ; J American Society of Echocardiography; vol. 10; No. 8; ppl 830-839; Oct. 1997.

Pratt, William K.; Digital Image Processing; John Wiley & Sons; New York; 1991.

Specht et al.; Deconvolution techniques for digital longitudinal tomography; SPIE; vol. 454; presented at Application of Optical Instrumentation in Medicine XII; pp. 319-325; 1984.

Specht, D.F.; Probabilistic neural networks; Pergamon Press; Neural Networks; vol. 3; pp. 109-118; 1990.

* cited by examiner

METHOD AND APPARATUS TO VISUALIZE THE CORONARY ARTERIES USING ULTRASOUND

CROSS REFERENCES TO RELATED APPLICATIONS

The present application claims the benefit of U.S. Provisional Patent Application Ser. No. 60/765,887, filed Feb. 6, 2006, (Feb. 6, 2006).

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention is generally related to medical ultrasound, and more particularly to a non-invasive screening method and apparatus for visualizing coronary arteries which solves artery curvature problems by projecting the three dimensional volume onto a two dimensional screen, highlighting the arteries and veins in contrast to other tissue and the heart chambers by using nonlinear techniques, storing many processed 2D slices into a 3D volume, and projecting the volume with varying view angles controlled by a pointing device.

2. Discussion of Related Art Including Information Disclosed Under 37 CFR §1.97, 1.98

In his well-respected textbook, *Echocardiography*, Harvey Feigenbaum, M.D., describes analysis techniques for many cardiac conditions. Most of these are used in routine clinical practice. An exception is the visualization of the coronary arteries (CAs) and assessment of their condition. Considering the seriousness of coronary artery disease, it is obvious that a non-invasive screening technique to assess obstruction in these arteries would be of great importance.

At pages 482-490 of *Echocardiography*, $5^{th}$ Edition, Feigenbaum shows 2D views of the coronary arteries. These studies prove that clinical ultrasound machines circa 1993 already had sufficient resolution to image the larger parts of these arteries. However, as Feigenbaum states, the curved nature of the arteries usually does not permit them to be seen for any length in an individual frame. In addition, it takes great skill and knowledge to recognize the arteries when they do come into view. For these reasons, clinical ultrasound is rarely used to visualize the CAs.

Because of the curved nature of the CAs, it would be advantageous and desirable to visualize them in three dimensions. The current patent teaches the steps required to achieve this goal.

Several U.S, patents and/or patent applications teach or show methods of imaging coronary arteries using ultrasound or other medical imaging techniques. Notable among them are U.S. patent application Ser. No. 2006/0079782, by Beach, et al., which shows an ultrasonic technique for visualizing coronary arteries using a 2-D scan and a 3-D display.

U.S. patent application Ser. No. 2006/0079759, by Vaillant, et al., discloses a method and apparatus for registering 3-D models of the heart using ultrasound.

U.S. patent application Ser. No. 2005/0281447, by Moreau-Gobard, et al., teaches a method of producing a 3-D image of the coronary artery system using ultrasound.

U.S. patent application Ser. No. 2005/0004449, by Mitschke, et al., teaches the use of ultrasound to acquire preoperative 3-D images for marker-less navigation of a medical instrument.

U.S. patent application Ser. No. 20020087071, by Schmitz, et al., teaches a process for graphic visualization and diagnosis of thrombi as well as the use of particle suspensions for the production of contrast media for the visualization of thrombi (circumscribed blood solidification that forms in arteries or veins by intravascular clotting) through the use of nuclear spin tomography. This method produces 3-D images from a 2-D source.

U.S. Pat. No. 6,148,095, to Prause, et al., shows a method of three-dimensional reconstruction of coronary arteries by fusing data between biplane angiography and IVUS frames of a pullback sequence. The 3D course of the tortuous vessel is first determined from the angiograms and then combined with the 2D representations regarding the 3D course (e.g., segmented IVUS frames of a pullback sequence) using a data fusion apparatus and method: The determination of the 3D pullback path is represented by the external energy of the tortuous vessel and the internal energy of a line object such as a catheter.

U.S. patent application Ser. No. 2005/0288588, by Weber, et al., discloses a method and apparatus for electronic volume data acquisition using ultrasound generates image data in a coherent aperture combining beamforming (CAC-BF) scanning and imaging process.

U.S. Pat. No. 6,166,853, to Sapia, et al., teaches use of an adaptive structure of a Wiener filter to deconvolve three-dimensional wide-field microscope images for the purposes of improving spatial resolution and removing out-of-focus light. The filter is a three-dimensional kernel representing a finite-impulse-response (FIR) structure requiring on the order of one thousand (1,000) taps or more to achieve an acceptable mean-square-error. Converging to a solution is done in the spatial-domain. Alternatively, a three-dimensional kernel representing an infinite-impulse-response (IIR) structure may be employed, as an IIR structure typically requires fewer taps to achieve the same or better performance, resulting in higher resolution images with less noise and faster computations.

The foregoing patents reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is a method and apparatus for providing three-dimensional images of the coronary arteries.

It is an object of the present invention to provide such three-dimensional images using ultrasound.

It is a further object of the present invention to provide a non-invasive screening test to assess the patency of the coronary arteries.

It is yet another object of the present invention to provide a new and improved means of evaluating the degree of obstruction in partially occluded arteries.

It is still another object of the present invention to provide a new and improved means to visualize coronary arteries which overcomes artery curvature problems by projecting the three-dimensional volume onto a two dimensional screen.

It is still another object of the present invention to provide improved three dimensional images of coronary arteries by utilizing linear filtering to reduce noise, using nonlinear techniques, such as neural networks, to highlight arteries and veins in contrast to other tissue and the heart chambers, storing numerous processed 2D slices into a 3D volume, and then projecting the volume with varying view angles controlled by a pointing device.

An even further object of the present invention is to provide gyroscopic stabilization to the ultrasound probe to minimize unwanted angulation during data collection.

The foregoing summary broadly sets out the more important features of the present invention so that the detailed description that follows may be better understood, and so that the present contributions to the art may be better appreciated. There are additional features of the invention that will be described in the detailed description of the preferred embodiments of the invention which will form the subject matter of the claims appended hereto.

Accordingly, before explaining the preferred embodiment of the disclosure in detail, it is to be understood that the disclosure is not limited in its application to the details of the construction and the arrangements set forth in the following description or illustrated in the drawings. The inventive apparatus described herein is capable of other embodiments and of being practiced and carried out in various ways.

Also, it is to be understood that the terminology and phraseology employed herein are for descriptive purposes only, and not limitation. Where specific dimensional and material specifications have been included or omitted from the specification or the claims, or both, it is to be understood that the same are not to be incorporated into the appended claims.

As such, those skilled in the art will appreciate that the conception, upon which this disclosure is based may readily be used as a basis for designing other structures, methods, and systems for carrying out the several purposes of the present invention. It is important, therefore, that the claims are regarded as including such equivalent constructions as far as they do not depart from the spirit and scope of the present invention. Rather, the fundamental aspects of the invention, along with the various features and structures that characterize the invention, are pointed out with particularity in the claims annexed to and forming a part of this disclosure. For a better understanding of the present invention, its advantages and the specific objects attained by its uses, reference should be made to the accompanying drawings and descriptive matter in which there are illustrated the preferred embodiment.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

The present invention is a method and apparatus that renders a projection of images of the coronary arteries in three dimensions using ultrasound. In its most essential aspect, this is accomplished by first producing a 3D array of voxels indicating the blood-filled areas of the heart. Next, a 2D image of the blood-filled areas is projected as a function of view angle and rotation, and this allows an observation and evaluation of the blood-filled areas from a number of view angles such that the coronary arteries and veins are seen unobscured by the major chambers of the heart. The objective is to provide a non-invasive screening test to assess the patency of the coronary arteries. It is hoped that in addition to detecting complete blockages of the arteries, it will also be possible to assess the degree of obstruction in partially occluded arteries.

Several methods are available to obtain the necessary three dimensional information using ultrasound. Two methods have been published concerning direct 3D. One is the RT3D method developed by Dr. Von Ramm and associates at Duke University (see, S. W. Smith, H. G. Pavy, and O. T. von Ramm, "High-speed ultrasound volumetric imaging-system. 1. Transducer design and beam steering," *IEEE Trans. Ultrason., Ferroelect., Freq. Contr.*, vol. 38, pp. 100-108, 1991; and O. T. von Ramm, S. W. Smith, and H. G. Pavy, "High-speed ultrasound volumetric imaging-System. 2. Parallel processing and image display," *IEEE Trans. Ultrason., Ferroelect., Freq. Contr.*, vol. 38, pp. 109-115, 1991.)

Another direct 3D method is the CAC-BF method patent pending by Weber et al. (discussed supra).

Neither of the above-referenced direct 3D methods provides sufficient resolution to reliably image the coronary arteries. One reason for this is that resolution is dependent on focusing of both the transmitted beam and the received energy. In order to capture a 3D image of the heart fast enough to freeze motion at a particular part of the cardiac cycle, the number of transmit pulses possible due to the speed of ultrasound in tissue is very limited. These pulses cannot be sharply focused if one is to cover the entire volume. Although no such limitation applies to the focusing of the received beam, the combination of transmit focusing and receive focusing is not as sharp as is possible with a 2D scanner. For this reason, the preferred implementation of the present invention is to utilize the superior resolution of 2D scanners and store a sufficient number of closely spaced 2D slices to capture the structural features of the coronary arteries and other portions of the heart H.

Figure 1:
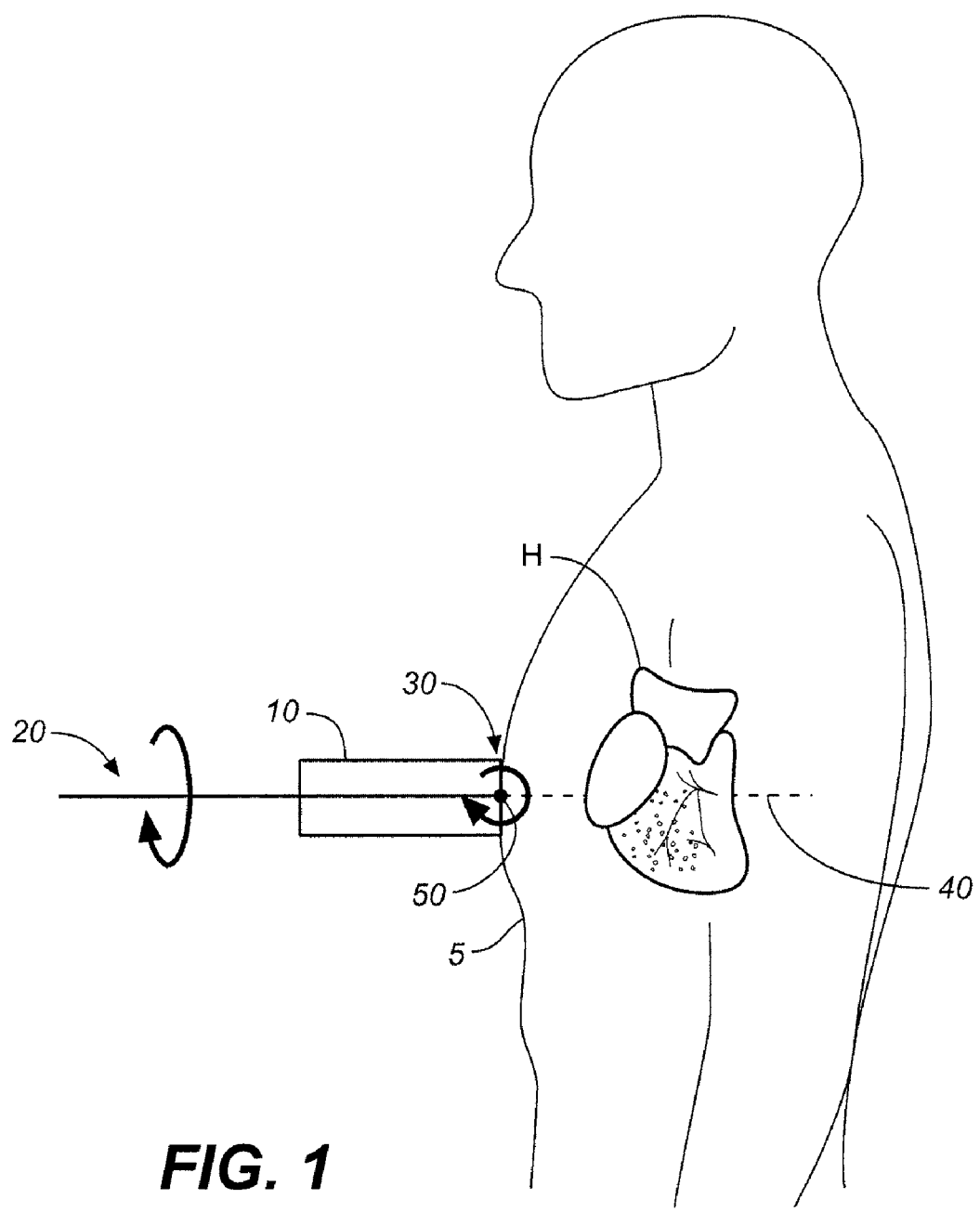
FIG. 1 is a schematic diagram illustrating probe angles discussed in the instant disclosure.

Referring now to FIG. 1, the slices can be obtained by a sequence of rotations of the probe 10 either in roll angle 20, or in pitch angle 30. In this context, roll angle means the degree of rotation about the central scan line of the 2D scanner 40, while pitch angle is the degree of rotation about the line 40 of the probe transducers, the end view of which is indicated by dot 50. In the case of a curved array, the line of probe transducers would be approximated by the least mean square fit line. Yaw angle is orthogonal to pitch and roll.

Several method steps are needed to capture the information and assemble it into a useful display. They are as follows:

First, an LMS adaptive filter or Wiener filter is used to remove aperture blur and speckle noise from each 2D image obtained. It is known that linear filtering can be very effective on 2D scans (see, in particular, Sapia, M. A., Fox, M. D., Loew, L. M., Schaff, J. C., "Ultrasound Image Deconvolution Using Adaptive Inverse Filtering", 12th IEEE Symposium on Computer-Based Medical Systems, CBMS 1999, pp. 248-253; Sapia, M. A., "Deconvolution of Ultrasonic Waveforms Using an Adaptive Wiener Filter," Review of Progress in Quantitative Nondestructive Evaluation, Volume 13, Edited by D. O. Thompson and D. E. Chimenti, New York, Plenum Press, pp. 855-862, 1994; Mark Angelo Sapia, "Multi-Dimensional Deconvolution of Optical Microscope and Ultrasound Imaging Using Adaptive Least-Mean-Square (LMS) Inverse Filtering," Ph.D. Dissertation, University of Connecticut, 2000; Specht, D. F., Blind deconvolution of motion blur using LMS inverse filtering, Lockheed Independent Research, unpublished, 1976); U.S. Pat. No. 6,166,853, to Sapia, et al.; U.S. patent application No. 2005/0053305, by Li et al). This step may not be necessary, as "standard" 2D scanners are constantly improving and may correct sufficiently for aperture blur.

Next, after collecting a sufficient number of closely spaced 2D slices to represent the structures of the heart in the vicinity of the CAs, this information is used to fill the voxels of a 3D array. It is also necessary to compensate for non-uniform sampling and jitter in the positioning of adjacent slices due to motion of the transducer and of the heart. Techniques to accomplish this are discussed in depth in Nadkarni, Seemantini, "Cardiac Motion Synchronization for 3D Cardiac Ultrasound Imaging," Ph.D. Dissertation, Univ. of Western Ontario, 2002, and Maria J. Ledesma-Carbayo et al, "Spatio-Temporal Nonrigid Registration for Ultrasound Cardiac Motion Estimation," IEEE Trans. on Medical Imaging, v24, No. 9, September 2005, both of which are incorporated in their entirety by reference herein.

Next, in order to accomplish the previous step it is necessary to record the position and angle of each 2D slice relative to the other slices. This can be accomplished by a fixture positioned rigidly above the patient's chest. However, the preferred embodiment of this invention allows the sonographer to scan manually in order to find the best view for a particular patient. The sonographer must take care to scan over the entire volume of interest. Redundant images are discarded or averaged. A sensor to record relative instantaneous positions of the probe may be attached to a standard handheld probe. A gyroscopic stabilizer attached to the probe is used to minimize angular variations except on the axis desired. The gyroscope also provides a reference for measuring the angular position of the probe. A sensor measures the position and provides this information to the computer.

Then, in order to acquire sufficient information for a 3D display, EKG gating or image-based synchronization is employed to capture the images at only one part of the cardiac cycle. Thus the total scan time will probably take many cardiac cycles. Nadkarni, cited above, shows that image-based synchronization is more reliable than the traditional EKG synchronization, but it is more complicated. Therefore image-based synchronization is an alternate method that may be employed.

Next, the images are segmented. Linear filtering may not be effective in the third dimension because the time between slices is necessarily large and the beating heart cannot be considered a stationary target. There will also be jitter displacement between adjacent slices. It is not an object of this invention simply to perform deconvolution of a point spread function in three dimensions (although this could be done).

Rather, as indicated above, it is an object of this invention to discriminate between blood-filled areas and other areas of tissue so as to display only the blood-filled areas. These will include, in addition to the main chambers of the heart, the coronary arteries and veins. It is a further object of this invention to separate the arteries and veins from everything else so that they can be studied in detail. The separation is accomplished by further discriminating between large blood-filled areas and narrow ones, such as arteries and veins, and displaying only the later. Several feedforward neural networks can be used for this step. All require training on examples of the two categories (e.g. blood-filled areas and other tissue). The most-popular neural networks to be used in this step include: (1) the Multi-Layer Perceptron (discussed in Simon Haykin, *Neural Networks: A Comprehensive Foundation*, 2nd Edition, Prentice Hall, 1999); (2) the Probabilistic Neural Network (variously considered in D. F. Specht, "Probabilistic Neural Networks." Neural Networks, vol. 3, pp 109-118, 1990; D. F. Specht, "Enhancements to Probabilistic Neural Networks," Proc. IEEE International Joint Conference on Neural Networks, Baltimore, Md., June, 1992; and D. F. Specht and H. Romsdahl, "Experience with Adaptive PNN and Adaptive GRNN," Proc. IEEE International Joint Conference on Neural Networks, vol. 2, pp. 1203-1208, Orlando, Fla., June 1994; and (3) the Support Vector Machine (discussed in Nello Cristianini and John Shawe-Taylor, *An Introduction to Support Vector Machines*, Cambridge University Press, 2000.

Alternatively, the broad categories of blood-filled areas and other tissue areas can be more specifically designated as tubular blood-filled areas vs. everything else, thereby letting the neural network suppress the large blood-filled areas of the chambers of the heart. It is important that neural networks are not limited to linear relationships. In addition to classification of each voxel as either a tubular blood-filled or not, image segmentation can be further enhanced by influence of neighbor pixels or voxels, as described in M. Morrison and Y. Attikiouzel, "A probabilistic neural network based image segmentation network for magnetic resonance images," in *Proc. Conf. Neural Networks*, Baltimore, Md., 1992, vol. 3, pp. 60-65. This paper describes an image segmentation process in which only neighboring pixels are considered, but neighboring voxels in the 3D representation can be used in the presently inventive ultrasound application.

Alternatively, discrimination between blood-filled tissues and other tissues can be accomplished using techniques such as Classification and Regression Trees (CART), Hidden Markov Models (HMM) or Fuzzy Logic. An efficient classifier is found in the latest version of the General Regression Neural Network, described in a paper authored by the present inventor, D. F. Specht, "GRNN with Double Clustering," Proc. IEEE International Joint Conference on Neural Networks, Vancouver, Canada, Jul. 16-21, 2006.

Finally, the point of view of the 3D image is rotated so that one group of coronary arteries at a time can be observed not obscured by the others or non-suppressed portions of the main chambers of the heart or other artifacts.

Linear filtering such as LMS or Wiener filtering is very effective when the point spread function of the imaging system is known and the object is stationary. The point spread function can be measured using a known tissue or wire phantom. These linear filtering techniques re effective when the object is reasonably stationary during a single 2D scan with duration on the order of $\frac{1}{30}$ second. However, the second condition does not apply for the time required to acquire a 3D volume. For this reason a linear deconvolution filter is not a good choice for the third dimension. An artificial neural network ("ANN") has the capacity to select the surrounding voxels that contribute to a reliable classification while rejecting the voxels that detract, and then weighting those that are intermediate. Clearly the voxels within a given 2D slice will have more relevance than the others, but significant information can be extracted from adjacent slices.

A second reason for using a nonlinear filter is that small echos from solid tissue and large echos from solid tissue, including specular reflections and speckle patterns, all must be displayed similarly as small values compared to those of the blood-filled areas. Although linear filtering with thresholding could accomplish this portion of the task, ANNs are inherently nonlinear.

The Wiener Filter: The Wiener filter is not new, but since it is important for the debluring step, it will be described briefly here in the context of the present invention.

The Wiener filter is the mean squared error optimal stationary linear filter for images degraded by additive noise and blurring. Wiener filters are usually applied in the frequency domain. Given a degraded image i(n,m), one takes the Discrete Fourier Transform (DFT) or the Fast Fourier Transform (FFT) to obtain I(u,v). The true image spectrum is estimated by taking the product of I(u,v) with the Wiener filter G(u,v):
$\hat{S}=G(u,v)I(u,v)$ The inverse DFT or FFT is then used to obtain the image estimate s(n,m) from its spectrum. The Wiener filter is defined in terms of these spectra:

H(u,v) Fourier transform of the point spread function (psf)
$P_s(u,v)$ Power spectrum of the signal process, obtained by taking the Fourier transform of the signal autocorrelation
$P_n(u,v)$ Power spectrum of the noise process, obtained by taking the Fourier transform of the noise autocorrelation The Wiener filter is:

$$G(u,v) = \frac{H*(u,v)P_s(u,v)}{|H(u,v)|^2 P_s(u,v) + P_u(u,v)}$$

The ratio $P_s/P_n$ can be interpreted as signal-to-noise ratio. At frequencies with high signal to noise ratio, the Wiener filter becomes $H^{-1}(u,v)$, the inverse filter for the psf. At frequencies for which the signal to noise ratio is low, the Wiener filter tends to 0 and blocks them out.

$P_s(u,v)+P_n(u,v)=|I(u,v)|^2$. The right hand function is easy to compute from the Fourier transform of the observed data. $P_n(u,v)$ is often assumed to be constant over (u,v). It is then subtracted from the total to yield $P_s(u,v)$.

The psf can be measured by observing a wire phantom in a tank using the ultrasound instrument. The Fourier transform of the psf can then be stored for later use in the Wiener filter when examining patients.

Because the psf is not constant as a function of range, the Wiener filter will have to be applied separately for several range zones and the resulting images will have to be pieced together to form one image for display. A useful compromise might be to optimize the Wiener filter just for the range of the object of interest such as a coronary artery or valve.

An Adaptive Inverse Filter: As pointed out by Sapia and Fox (1999), an adaptive filter in the spatial domain is essentially equivalent to the Wiener Filter implemented in the frequency domain and has some additional advantages. The main advantages are the simplicity of the algorithm, and that, being adaptive, it minimizes sources of noise such as edge effects in addition to deconvolution of blurring resulting from the point spread function of the system.

Figure 2:
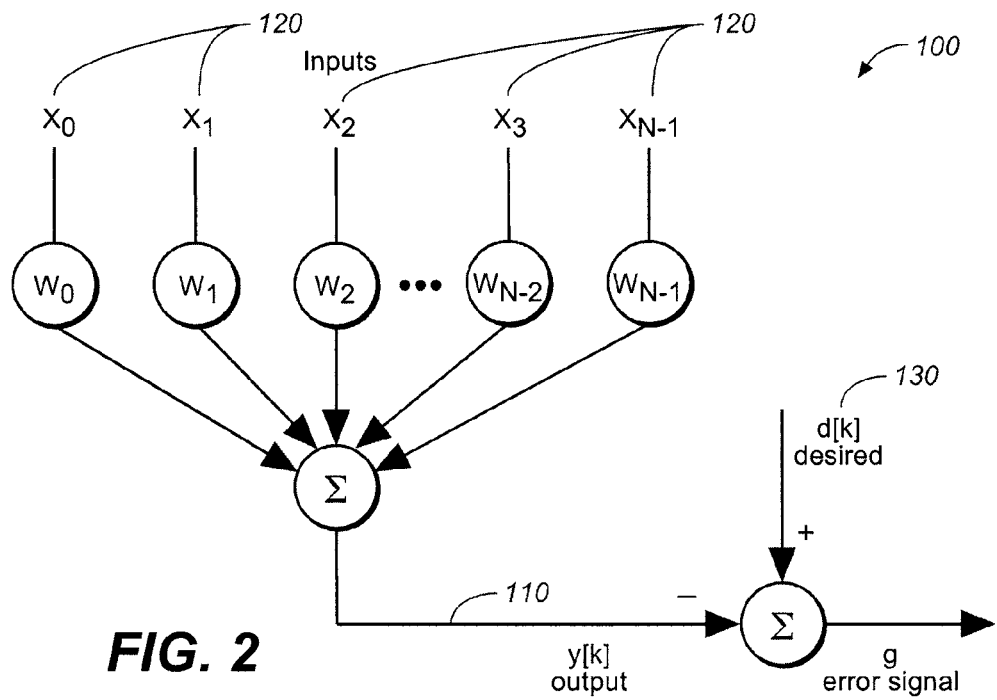
FIG. 2 is a schematic block diagram showing a linear combiner.

In the spatial domain a transversal filter 100 as in FIG. 2 is used to produce an improved signal y 110 as a weighted average of a finite number of inputs $x_0$ through $x_{n-1}$ 120. In the case of ultrasound, the greatest blurring is transverse to the direction of the beam and so the most significant improvement will be in this direction. For this reason, all of the inputs, x, may be taken centered around the pixel y to be estimated and from the same distance from the transducer (e.g. from the same line in the transverse direction). The same algorithm applies without change if some of the x's are taken from adjacent transverse lines. The method to solve for the optimum weight vector is to use an adaptive least-mean-square (LMS) algorithm. The LMS solution converges numerically to the optimum solution.

Let $X_k$ be a N-dimensional vector of the inputs used for estimating y[k], and let $W_k$ be the set of weights after training k samples. The linear estimate when trained will be $y[k]=X_k^T W$.

For training it is necessary to know the desired value of the output pixels, d[k] 130. These can be obtained by imaging a phantom with known geometry. After each training iteration, the error can be evaluated as $$\xi_k = d[k] - X_k^T W_k.$$

The LMS algorithm in equation form is:

$$W_{k+1} = W_k + 2\mu \xi_k X_k$$

where μ is the convergence coefficient. [See B. Widrow and S. D. Stearns, *Adaptive Signal Processing*, Englewood Cliffs, N J, Prentice-Hall, pp. 99-137, 1985.]

Because the psf is not constant as a function of range, the adaptive inverse filter also will have to be applied separately for several range zones and the resulting images will have to be pieced together to form one image for display.

Figure 3:
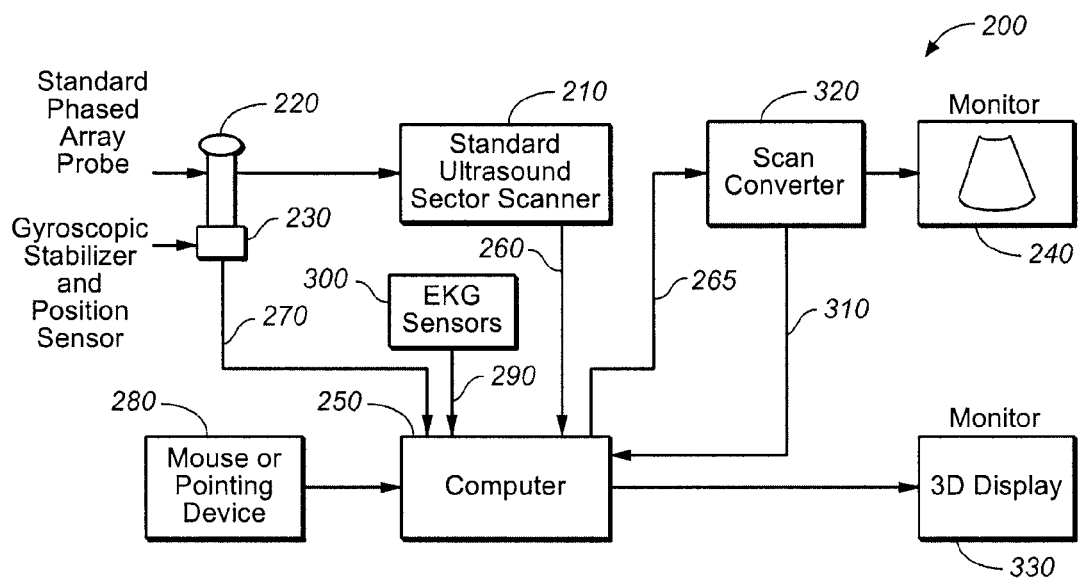
FIG. 3 is a schematic block diagram showing the essential components comprising the inventive apparatus.

Required Hardware: A typical hardware system 200 incorporating the invention is shown in FIG. 3. The central component is a standard cardiac ultrasound scanner 210 with its scan converter 320 and monitor 240 such as those marketed by Siemens, General Electric, Philips, or Toshiba.

The standard scanner includes a phased array probe 220 shown separately. Mechanically attached to the probe is a gyroscopic stabilizer and position sensor 230 which must, at minimum, measure the relative angle of the probe as it is rotated to insonify the volume of the heart. For the purpose intended, it need not insonify the entire heart muscle, but only the main coronary arteries. The angle could be referenced to a stationary fixture. However, because only the angle is required, the reference can be a gyroscope attached to the probe. Small variations in the location of the probe from one scan to the next can be compensated by software using correlation or related techniques. A more-complex model could use integrating accelerometers to maintain exact position information.

The output of the standard scanner is displayed on a monitor 240. The display typically has several modes including 2D sector, M mode, and doppler.

A computer 250 is necessary to implement the software algorithms described. Inputs to the computer include the processed scan line returns 260 from the sector scanner, the position sensors 270 mentioned above, some sort of pointing device such as a mouse 280, and usually electrocardiogram sensor input 290 from an EKG sensor 300 for synchronization. The scan line information needed for LMS filtering or Wiener filtering is that of individual scan lines after beam formation but before scan conversion for display. The scan line information needed for discrimination, classification, and segmentation is the output 310 of the scan converter 320 because dimensions are constant after this conversion. After discrimination, classification, and segmentation, a 3D image is displayed on a monitor 330.

FIG. 3 shows the components necessary for an add-on (after market) system. In this figure, the scan converter is shown separate from the rest of the unit to indicate that the add-on computer optionally would tap into the scan line information before scan conversion and then return deconvolved scan line information to the scan converter. However, much integration is possible. In practice, the two separate monitors could actually be the same monitor with 3D display as a separate mode. Standard ultrasound sector scanners typically include EKG amplifiers, so there is no need to duplicate these. Standard ultrasound sector scanners always include a computer. That computer and the computer component shown could be combined into one computer with both sets of software integrated.

An alternative and simpler configuration consists of leaving the outputs 260 connected to the inputs 265 as in a standard cardiac ultrasound system. In this case, the inputs used for LMS or Wiener filtering would be the output of the scan converter 310. The computer would resample along curved lines both for finding psfs and for performing the deconvolution operation.

Figure 4:
FIGS. 4 and 5 are screen shots showing simulated three-dimensional displays of the coronary arteries.
Figure 5:
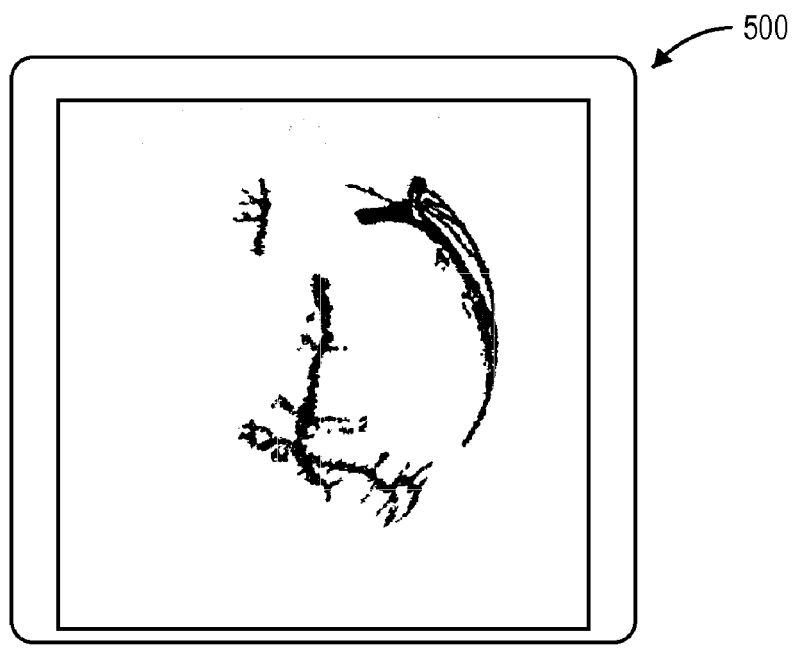

Simulated Display: Using the inventive method, a simulated representation of the coronary arteries and veins has been formed in a three dimensional format. Two dimensional projections have been formed under control of a mouse to select view angles to best highlight the areas of interest. Results from two particular view angles 400, and 500, respectively, are reproduced in FIGS. 4 and 5. In FIG. 4 the volume was rotated to show the left coronary artery, the bifurcation to anterior descending and to circumflex branch. Parallel to both branches is the great cardiac vein. In FIG. 5 the volume was rotated to show the right coronary artery.

Gyroscopic Stabilization and Angle Measurement: When collecting data for a 3D presentation, it is important to control the position of the phased array transducers while the probe is being rotated. Otherwise the spatial position (x, y, and z) and the angular position (pitch, yaw, and roll) must be continuously measured and compensated for by software. The fixture mounted over the patient, mentioned in the previous section, can assure that of the six degrees of freedom, all are fixed during the collection of data except either roll or pitch, which is intentionally changed and measured. Some compensation for spatial position will still have to be done (perhaps by correlation techniques) because of the motion of the heart. The fixture satisfies the technical requirements for the instrumentation, but sacrifices the convenience that comes with hand positioning of the probe to find the best view for a particular patient.

A preferred embodiment of the probe for this invention includes the following: First and second gyroscopes mechanically attached to a standard phased array probe designed for two dimensional scans. The first gyroscope is aligned with the center line of the sector scan (i.e., perpendicular to the surface of the skin and aimed at the tissue to be imaged). The second gyroscope is mounted perpendicular to the alignment of the first gyroscope with a sensor to measure the relative angle between it and the probe handle as it is mechanically rotated.

The first gyroscope is motorized and has sufficient mass and rotational speed to stabilize the handheld probe in pitch and yaw even though the technician's hand might apply slight pressure to twist it in pitch or yaw. The second gyroscope can be much smaller in mass (or it could be solid state, such as piezoelectric) as its only function is to measure the rotation angle of the probe.

In operation, the gyroscopes would initially be turned off while the technician positions the probe to find the cone which best contains the volume of interest. When he or she is satisfied with the orientation of the probe, he or she turns on the gyroscopes to stabilize that orientation and then scans through the range of rotation angles (180 degrees covers the entire cone, but a more limited range may be sufficient). The scanning through rotation angles may be done by hand or it could be automated.

An alternate embodiment of the probe for this invention includes the following: First and second gyroscopes mechanically attached to a standard phased array probe designed for two dimensional scans. The first gyroscope is aligned parallel to the line of transducer elements in the probe (or the closest mean-squared-error fit line in the case of a curved array) it is not instrumented for angle measurement. The second gyroscope is mounted perpendicular to the alignment of the first gyroscope with a sensor to measure the relative angle between it and the probe handle.

The first gyroscope is motorized and has sufficient mass and rotational speed to stabilize the handheld probe in yaw and roll, even though the technician's hand might apply slight pressure to twist it in yaw and roll. For these purposes, pitch angle is defined as angle of rotation about the axis of the first gyroscope. The second gyroscope can be much smaller in mass (or it could be solid state, such as piezoelectric) as its only function is to measure the pitch angle.

In operation, the gyroscopes would initially be turned off while the technician positions the probe to find the best range of views. When he or she is satisfied with the orientation of the probe, he or she turns on the gyroscopes to stabilize that orientation and then scans through the range of pitch angles.

Another implementation of the probe is to have a two dimensional array of phased array transducers so that the angles can be adjusted electronically.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:
1. A method of reconstructing a 3D image, comprising the steps of:
   (a) scanning heart and surrounding tissue with a 2D ultrasound scanner;
   (b) recording a succession of 2D scans to image the heart tissue;
   (c) filling a plurality of voxels of a 3D array with the recorded 2D scans;
   (d) applying an artificial neural network to classify the voxels of the 3D array by selecting voxels representing blood-filled areas of the heart tissue and rejecting voxels representing non blood-filled areas of the surrounding tissue;

(e) discriminating between arteries and veins of the heart tissue and chambers of the heart; and (f) displaying the arteries and veins of the heart tissue.

2. The method of claim 1, wherein step (a) is performed using a handheld medical ultrasound probe.

3. The method of claim 2, further including the step of stabilizing the medical ultrasound probe with a gyroscopic stabilizer to hold the position of the medical ultrasound probe fixed in pitch and yaw such that it can be rotated with minimal changes in pitch and yaw.

4. The method of claim 3, wherein steps (b) and (c) are performed using a computer, and further including the step of measuring a rotation angle of the medical ultrasound probe with a gyroscope and sending the measurements to the computer.

5. The method of claim 2, further including the step of stabilizing the medical ultrasound probe with a gyroscopic stabilizer to hold the position of the medical ultrasound probe fixed in yaw and roll such that it can be rotated with minimal changes in yaw and roll.

6. The method of claim 5, wherein steps (b) and (c) are performed using a computer, and further including the step of measuring a rotation angle of the medical ultrasound probe with a gyroscope and sending the measurements to the computer.

7. The method of claim 2, further including the step of mounting the handheld medical ultrasound probe in a fixture above the patient and recording a position and angle of each of the succession of recorded scans.

8. The method of claim 2, further including the steps of:

(g) monitoring a position of the handheld medical ultrasound probe; and (h) sending an electrocardiogram lead to a computer for EKG gating.

9. The method of claim 1, further including the step of using a Wiener Filter to minimize image blur and noise from the succession of scans.

10. The method of claim 1, further including the step of using an adaptive inverse filter to minimize image blur and noise from the succession of scans.

11. The method of claim 1, wherein inputs to the artificial neural network are pixel values from a 2D scan.

12. The method of claim 1, wherein inputs to the artificial neural network are voxel values from a volume array interpolated from the succession of 2D scans.

13. The method of claim 1, further including the step of enhancing segmentation of blood-filled areas by weighting the classification of adjacent pixels or voxels.

14. The method of claim 1, wherein step (e) is accomplished using Classification and Regression Trees.

15. The method of claim 14, further including the step of enhancing segmentation of blood-filled areas by weighting the classification of adjacent pixels or voxels.

16. The method of claim 1, wherein step (e) is accomplished using Hidden Markov Models.

17. The method of claim 16, further including the step of enhancing segmentation of blood-filled areas by weighting the classification of adjacent pixels or voxels.

18. The method of claim 1, wherein step (e) is accomplished using Fuzzy Logic.

19. The method of claim 18, further including the step of enhancing segmentation of blood-filled areas by weighting the classification of adjacent pixels or voxels.

20. The method of claim 1, wherein step (f) includes a 3D image on a screen of only the arteries and veins of the heart tissue.

21. The method of claim 20, further including the step of controlling an angle of view of the 3D image with a computer input device.

22. The method of claim 20, wherein said displaying step displays the 3D image of the arteries and veins of the heart tissue highlighted in intensity or color and superimposed on echos showing the heart and surrounding tissue.

23. The method of claim 22, further including the step of controlling an angle of view of 3D image with a pointing device or other input.

* * * * *